United States Patent
Sernetz et al.

(10) Patent No.: US 7,481,651 B2
(45) Date of Patent: Jan. 27, 2009

(54) ORTHODONTIC DEVICE

(75) Inventors: Friedrich Sernetz, Pforzheim (DE); Walter Ehrenberger, Kaempfelbach (DE); Rainer Weber, Karlsbad (DE); Klaus Wigger, Neulingen (DE)

(73) Assignee: Dentaurum J.P. Winkelstroeter KG, Ispringen (DE)

( * ) Notice: Subject to any disclaimer, the term of this patent is extended or adjusted under 35 U.S.C. 154(b) by 0 days.

(21) Appl. No.: 11/319,049

(22) Filed: Dec. 27, 2005

(65) Prior Publication Data

US 2006/0172248 A1    Aug. 3, 2006

Related U.S. Application Data

(63) Continuation of application No. PCT/EP2004/007263, filed on Jul. 3, 2004.

(30) Foreign Application Priority Data

Jul. 4, 2003    (DE)  ................. 103 30 219

(51) Int. Cl.
*A61C 3/00* (2006.01)
(52) U.S. Cl. ...................................... 433/10
(58) Field of Classification Search ............ 433/10, 433/11, 13, 14, 17
See application file for complete search history.

(56) References Cited

U.S. PATENT DOCUMENTS

| | | | | |
|---|---|---|---|---|
| 2,019,773 A * | 11/1935 | Wirt | ............... | 433/11 |
| 2,236,042 A * | 3/1941 | Terwilliger | ............... | 433/14 |
| 3,494,034 A * | 2/1970 | Kesling | ............... | 433/17 |
| 3,838,514 A | 10/1974 | Polak | | |
| 4,927,362 A | 5/1990 | Snead | | |
| 5,094,614 A * | 3/1992 | Wildman | ............... | 433/14 |
| 5,322,435 A * | 6/1994 | Pletcher | ............... | 433/11 |
| 5,356,288 A | 10/1994 | Cohen | | |
| 5,613,850 A | 3/1997 | Wildman et al. | | |
| 5,630,715 A * | 5/1997 | Voudouris | ............... | 433/8 |
| 5,913,680 A | 6/1999 | Voudouris | | |
| 6,042,373 A * | 3/2000 | Hermann | ............... | 433/13 |
| 6,193,508 B1 * | 2/2001 | Georgakis | ............... | 433/11 |

(Continued)

FOREIGN PATENT DOCUMENTS

EP    0 453 250    10/1991

(Continued)

*Primary Examiner*—John J Wilson
(74) *Attorney, Agent, or Firm*—Lipsitz & McAllister, LLC

(57) ABSTRACT

To create an orthodontic device with a base having a base surface for fixing the device to a tooth, and a slot for receiving an archwire, which is defined by a bottom surface and two side surfaces arranged on either side of the bottom surface and aligned in substantially parallel spaced relation to each other, and which extends in a substantially straight line through the base in the longitudinal direction of the base on a side thereof facing away from the base surface, and with a cover element for at least partially covering the open side of the slot facing the bottom surface, which is convertible and is easier to handle during the conversion, and which offers the wearer an increased degree of security, it is proposed that the side surfaces of the slot have a positively locking guide, which is aligned substantially parallel in relation to the longitudinal direction of the slot, and in which the cover element is slidably and detachably held on the base.

25 Claims, 6 Drawing Sheets

U.S. PATENT DOCUMENTS

| | | |
|---|---|---|
| 6,887,075 B2 * | 5/2005 | Kawaguchi et al. ........... 433/17 |
| 7,033,170 B2 * | 4/2006 | Cordato ........................ 433/10 |
| 2005/0069833 A1 * | 3/2005 | Chikami ........................ 433/9 |

FOREIGN PATENT DOCUMENTS

| | | |
|---|---|---|
| WO | 2004/047665 | 6/2004 |
| WO | 2004/060193 | 7/2004 |

* cited by examiner

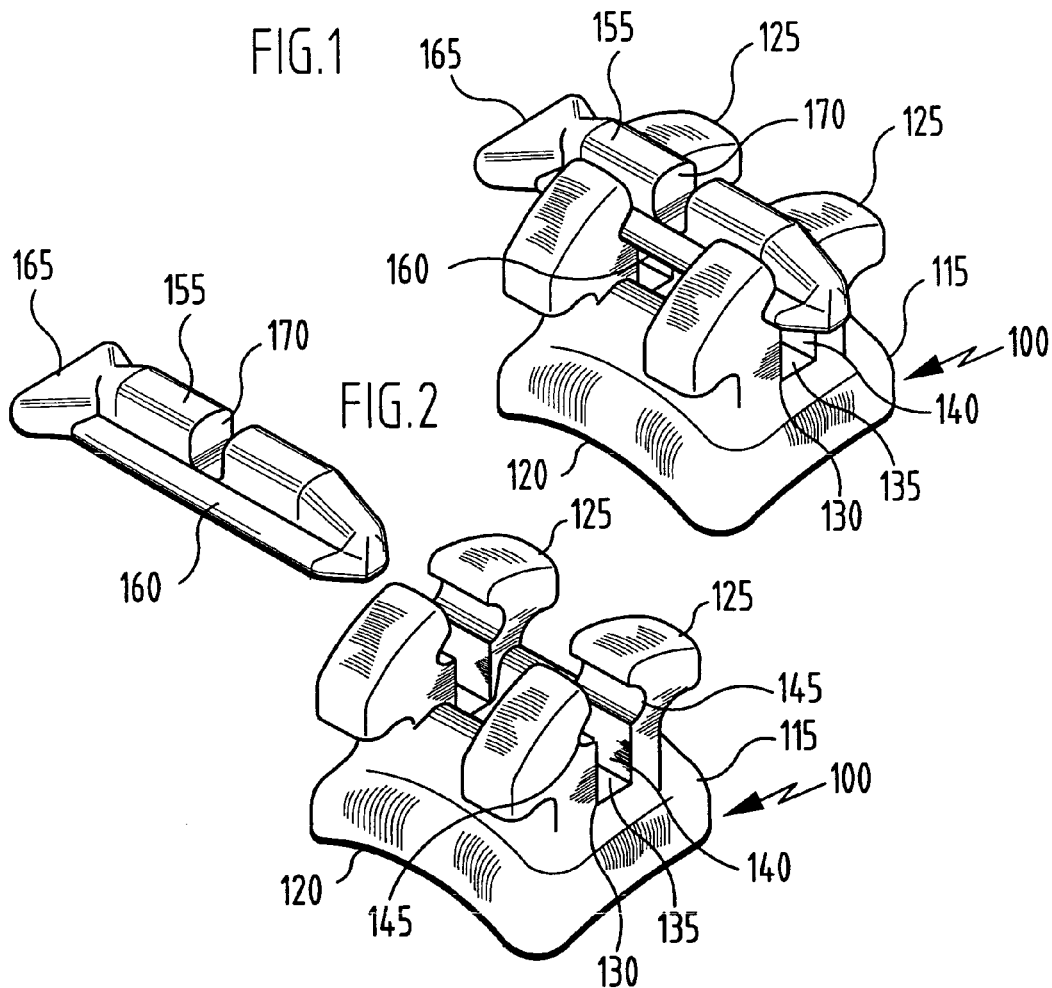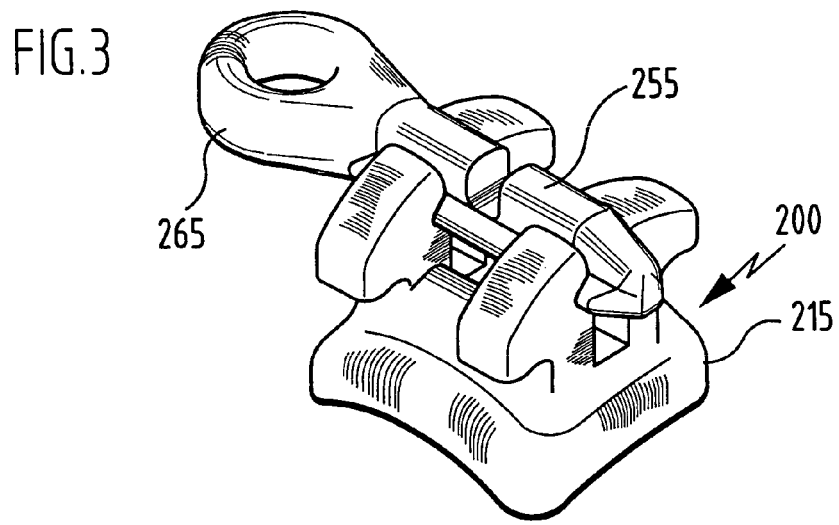

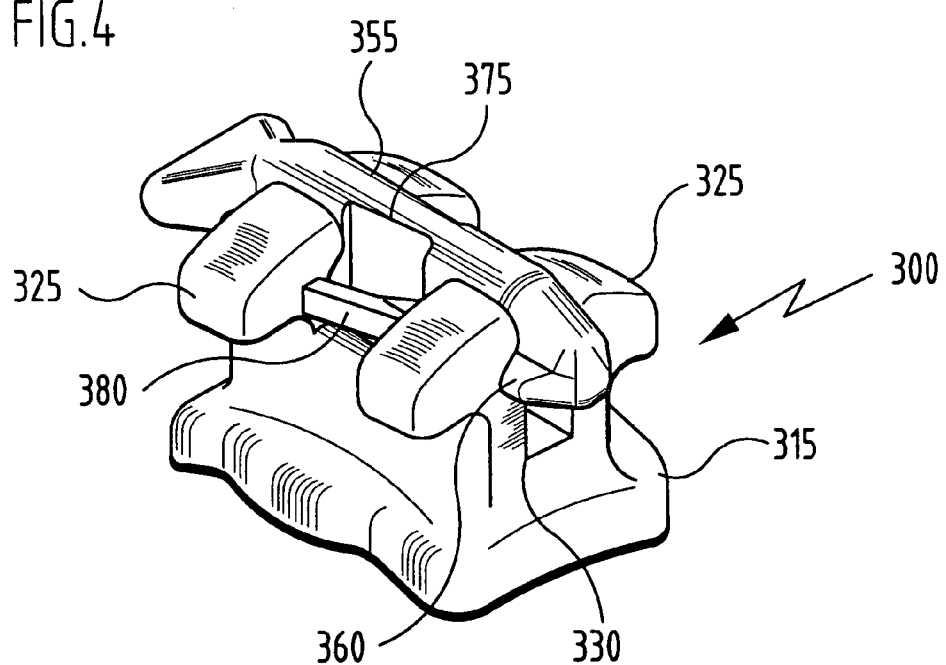
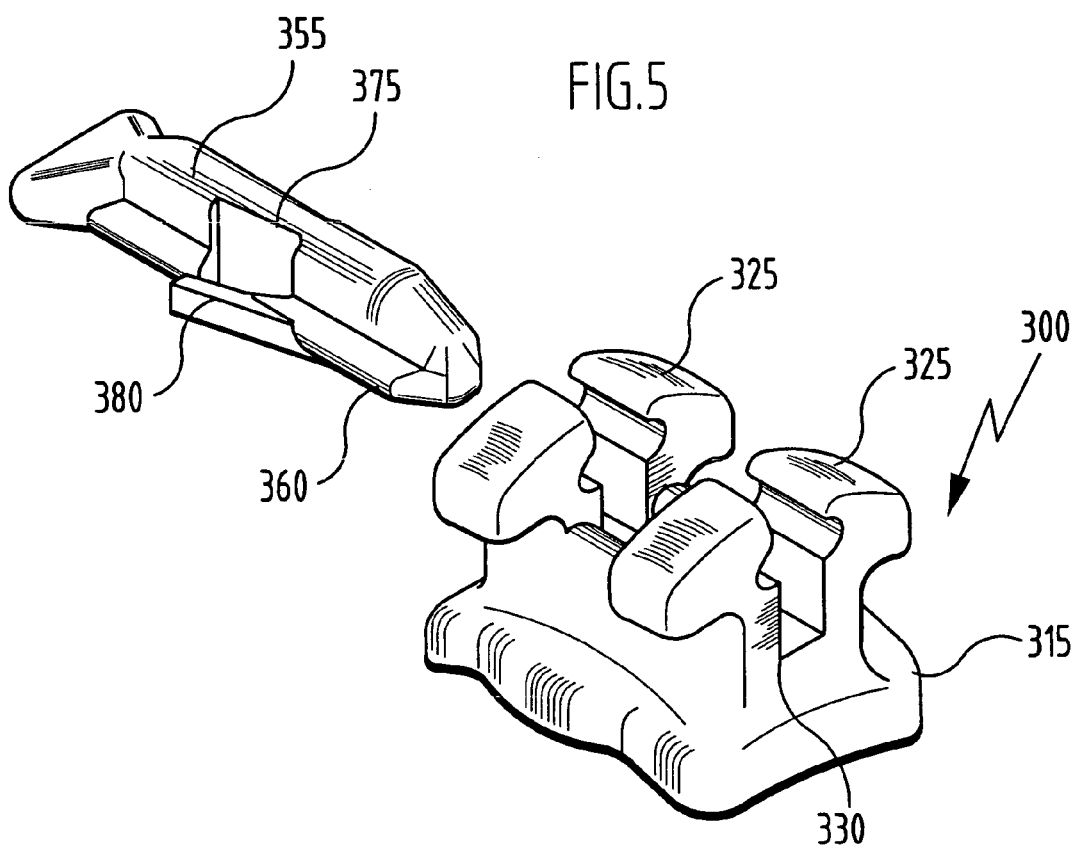

US 7,481,651 B2

ORTHODONTIC DEVICE

This application is a continuation of international application number PCT/EP2004/007263 filed on Jul. 3, 2004.

The present disclosure relates to the subject matter disclosed in international application number PCT/EP2004/007263 of Jul. 3, 2004 and German application number 103 30 219.0 of Jul. 4, 2003, which are incorporated herein by reference in their entirety and for all purposes.

BACKGROUND OF THE INVENTION

The invention relates to an orthodontic device with a base having a base surface for fixing the device to a tooth, and a slot for receiving an orthodontic archwire, which is defined by a bottom surface and two side surfaces arranged on either side of the bottom surface and aligned in substantially parallel spaced relation to each other, and extends in a straight line through the base in the longitudinal direction of the base on a side thereof facing away from the base surface, and with a cover element for at least partially covering the open side of the slot facing the bottom surface, wherein the side surfaces of the slot have a positively locking guide, which is aligned substantially parallel in relation to the longitudinal direction of the slot, and in which the cover element is slidably and detachably held on the base.

Such devices are used in orthodontics as special embodiments of so-called buccal tubes or brackets.

Buccal tubes are understood as being orthodontic attachment elements, which in the area of the lateral teeth serve to transmit the forces generated, for example, by archwires to the teeth. To this end, the buccal tubes are usually welded onto orthodontic bands, i.e., thin-walled metal rings, which are then pressed onto the crowns of the teeth and firmly cemented there. Alternatively, buccal tubes may also be adhesively bonded directly to the teeth.

Buccal tubes of this kind are also used on the so-called first molars, which, in youngsters at an age of usually less than twelve years, are understood as being the rearmost molars in the upper and lower jaws. The buccal tubes are used there for receiving an orthodontic archwire, which, as a rule, extends from the first molar on the left jaw side to the first molar on the right jaw side in the lower or upper jaw.

Brackets are understood as being orthodontic attachment elements, which are used from the incisors to and including the premolars in the upper and lower jaws and serve there to transmit the forces generated by archwires to the teeth. To this end, the brackets are usually secured to the teeth by means of an adhesive.

According to the conventional definition of buccal tubes and brackets, in the case of brackets the archwires are placed therein, whereas in the case of buccal tubes the archwires are slid in.

In order to intentionally move teeth during orthodontic treatment, archwires are inserted into the slots of brackets or into the openings of buccal tubes. If an archwire disposed in a bracket is twisted out of its position of rest by a misalignment of a tooth, it exerts by way of its elastic spring characteristics a force or a torque on the bracket or buccal tube and hence on the tooth. Whereas in the area of the brackets such archwires are inserted into slots provided therefor and held in the slot by means of thin wire ligatures or elastic plastic ligatures, there is no open slot in a buccal tube for receiving the archwire, but an opening, which may be in the form of a four-edged- or through-bore so that the orthodontist does not have to fix any ligatures to the buccal tube in the area of the molars, which is difficult to access.

If the orthodontic treatment includes the second molars, which in young patients usually break through later than the first molars, the buccal tubes are also attached to the second molars lying behind the first molars. In this case, it is advantageous for the orthodontist if the opening of the buccal tubes placed on the first molars is in the form of a slot.

Replacement of a buccal tube with a bracket usually requires removal of the cemented band to which the buccal tube is attached and reattachment of the bracket. This involves a great amount of work for the orthodontist and increases the risk of damaging the patient's tooth enamel. In order to avoid this, so-called convertible buccal tubes, which can be converted to a bracket by removing the wall of the through-bore on the buccal side, have already been used on the first molars.

In U.S. Pat. No. 3,838,514, a bracket is described, whose slot is covered on the buccal side by a cover element, which is fixed to the bracket by spot welds or braze points. Therefore, this bracket can also function as buccal tube.

Manufacture of brackets of such convertible design is relatively costly, as the bracket has to be joined to the cover element in a separate manufacturing step, for example, by welding or soldering. Moreover, with this joining technology, the amount of force for releasing the cover element from the bracket can only be inaccurately determined beforehand.

In U.S. Pat. No. 5,913,680, a bracket is described whose slot is closable by a small plate-shaped spring member. To this end, a side rim of the spring member engages a groove disposed in a side surface of the slot, while the side of the spring member opposite the side rim embraces wing members of the bracket.

In order that the spring member will be removable from the bracket with an acceptable amount of force, the spring member must be of correspondingly thin design, and the spring member, therefore, has sharp-edged rim areas, which increase the risk of injuring the wearer of the bracket.

A convertible buccal tube made of sintered metal and of integral design is known from U.S. Pat. No. 4,927,362. The buccal tube has a base for attachment to a tooth, and an elongated slot extends therethrough for reception of an archwire. The slot opening on the buccal side is covered by a cover plate which extends transversely over the cheek-facing side of the slot. The cover plate is integrally joined to the buccal tube adjacent the opposite side surfaces of the slot by elongated webs which extend along the entire length of the slot and have a smaller thickness than the cover plate. To open the slot, the cover plate has to be sheared from the buccal tube along both of the webs. The buccal tube may then be used as a normal bracket.

When severing the cover plate, undefined breakage locations and burrs remain on the buccal tube and may impede insertion of an archwire into the opened slot.

The object underlying the invention is, therefore, to create an orthodontic device of the kind mentioned at the outset, which is convertible, offers the wearer thereof an increased degree of security, and is easier to handle during the conversion without any special instruments.

This object is accomplished with an orthodontic device of the generic kind, in accordance with the invention, in that the positively locking guide is formed by two grooves disposed in side surfaces of the slot facing each other, and in that the cover element is of flat configuration at the side facing the bottom surface of the slot and has two guide elements, which are of complementary design to the grooves and engage the grooves in a positively locking manner.

The orthodontic device according to the invention offers the wearer thereof an increased degree of security and is easier to handle for the orthodontist in charge, as no undefined breakage locations and/or burrs are created when removing the cover element from the base, that might impede insertion of an archwire into the opened slot. The archwire is nevertheless securely held in the slot.

Therefore, the device according to the invention can be converted in a very simple way into a device with bracket function by the cover element being removed from the base in the longitudinal direction of the slot. The conversion may be reversed again by sliding the cover element in again. The converting procedure may be repeated virtually any number of times. This opens up new dimensions for the devices according to the invention by, for example, wingless brackets being made possible, with which the archwire in the slot of the bracket is held securely in the slot by a cover element instead of by ligatures anchored on wings.

Moreover, forces which must be applied when converting the device act substantially parallel to the base surface, so that the danger of inadvertently tearing the device off the tooth is minimized. Also, the devices according to the invention can be converted with precisely predeterminable forces, so that, again, the risk for the patient is reduced.

Furthermore, the device according to the invention is of two-piece design, and, therefore, its manufacture is more cost-effective, because injection molds with a simpler shape may be used.

The device according to the invention may be used both as buccal tube and as convertible buccal tube or as bracket on teeth other than molars, in which an archwire is ligatable by means of the cover element.

In accordance with the invention, the positively locking guide is formed by two grooves facing each other, which are disposed in side surfaces of the slot that face each other. The cover element has in the longitudinal direction two guide elements spaced from each other, which are of complementary design to the grooves and engage the grooves with positive locking. It is thereby ensured that the cover element is held on both sides of the slot and thus in a stable manner. In accordance with the invention, the cover element is of flat configuration at the side facing the bottom surface. It is thereby ensured that an archwire can come to rest against the bottom surface of the slot and against the cover element, so as to transfer the forces emanating from the archwire onto the base and from there onto the tooth to be treated. To ensure that the archwire can rest securely on the bottom surface and on the cover element, the cover element may have on the side facing the bottom surface of the slot a rib which projects into the slot.

If the device according to the invention is to be used as convertible buccal tube or as buccal tube, it is particularly advantageous for the grooves forming the positively locking guide to be aligned in parallel with the bottom surface of the slot, as an area of the bottom surface of the slot that is as large as possible can thus serve in a simple way as contact surface for the archwire to be inserted into the base.

The grooves forming the positively locking guide preferably extend at an acute angle to each other, so that the cover element can be wedged in the inserted position and, therefore, secured in this position.

Furthermore, the grooves may also be inclined at an acute angle to the bottom surface of the slot, so that upon inserting the cover element after placement of the archwire, the archwire can be secured with a clamped fit in the slot.

The slot is often of rectangular cross section transversely to its longitudinal direction, and the side surfaces defining the slot are usually of flat design. It is thereby ensured that the forces acting from a rectangular archwire are transmitted onto the base of the device and from there onto the tooth to be treated.

The cover element of the device according to the invention may be insertably and releasably held on the base, for example, by force locking, in particular, by friction locking. In accordance with an embodiment of the device according to the invention, which is preferred because it is easy to handle, the cover element in the completely inserted state is secured by a clamped or press fit in the positively locking guide on the base.

The cover element held on the base may be additionally provided with a receiver for a securing element, with which the cover element may be secured to the device in the fully inserted state. The cover element may be fixed, for example, by means of a wire or a ligature via the receiver to the base of the device.

Alternatively or additionally, the cover element may be provided with a locking element for securing the cover element to the base in the fully inserted state. Locking of the cover element to the base is achieved by, for example, a locking element engaging a cut-out provided on the base. To release the locking, the cover element may be provided with a recess into which the locking element is lowerable. Alternatively, the locking element may also be made of elastic material, so that upon removal of the cover element from the device, the locking element undergoes deformation and thus becomes disengaged.

In accordance with an advantageous embodiment of the device according to the invention, the cover element comprises a headpiece for gripping and removing the cover element. The headpiece may be arranged either at one end of the cover element or on the side of the cover element facing away from the slot so as to remove, for example, by hand, the cover element from the device or slidably insert the cover element by hand into the positively locking guide.

The headpiece may, for example, also be in the form of a hook or an eyelet. The cover element may thus be removed from the device or inserted into the slot of the base with, for example, a dental instrument.

It may be provided that one guide element or both guide elements of the cover element are interrupted in the longitudinal direction and do not extend over the entire length of the cover element. This has the advantage that when inserting the cover element, it can be guided more easily into the quite narrow space from the adjacent bracket as the cover element does not have to be inserted fully from the side owing to the interruption in the guide elements, but may first be inserted over approximately half of the length from the buccal side into the slot and subsequently slid sideways into the end position.

In order to keep the risk of injury to a wearer of the device according to the invention or even just irritations as low as possible, the cover element preferably has rounded edges on all sides thereof.

The cover element preferably has a veneer element for veneering the side of the base facing away from the base surface. The veneer element is preferably tooth-colored and can, therefore, conceal any aesthetically disadvantageous appearance of the base.

In a further preferred embodiment of the invention, it is provided that the cover element has at its front end in the direction of insertion a projection which in the inserted state protrudes out of the slot of the base.

This projection is preferably designed so as to be deformable, in particular thermoformable, in the inserted state.

Owing to the deformation of the projection, it can be designed as a mechanical securing element which, in addition to the force locking and positive locking between cover element and base prevents the cover element from becoming unintentionally detached from its fitting in the slot of the base. This may prove advantageous in a number of applications where the device is subjected to particular mechanical stress.

Alternatively, possibly after deformation, the projection may also be joined to the base of the device, for example, by laser welding, adhesive bonding, etc.

It is particularly simple when both the base and the cover element consist of metal, with, for example, spot welding by means of laser then resulting in a joint with a substance-to-substance bond between the cover element or its projection and the base.

When the cover element is to be removed from the slot again, this joint can then be simply released and the deformation of the projection reversed, so that the cover element can then be removed from the base without any difficulty.

In a variant, the deformation of the projection may be carried out by it being expanded in the area of a notch or a slot in the projection. The cover element is thereby prevented from being readily pulled out of the slot again. The expanded portion then forms a mechanical securing element here. The expanded portion may also be additionally joined to the base with a substance-to-substance bond by adhesive bonding, spot welding, etc., and, as mentioned hereinabove, this joint may, in turn, be simply released or broken, for example, with an instrument.

The device according to the invention may be configured both as bracket and as buccal tube.

To enable fixing of the device according to the invention to a tooth as simply as possible, the base surface of the base has a shape that is adapted to the corresponding tooth. To this end the base surface has a surface portion which is curved in one direction or in several directions.

The base of the device according to the invention may be made, for example, of metal, ceramics, plastic and/or reinforced plastic.

Like the base, the cover element may also be made of metal, ceramics, plastic and/or reinforced plastic, and, in view of aesthetic considerations, the material for the cover element may be selected independently of whatever material the base of the device is made from. It is particularly preferred for the cover element to be made of metal and/or plastic. In these cases, it is particularly easy to produce a mechanical securing element as described hereinabove. The following description of preferred embodiments of the invention serves in conjunction with the drawings to explain the invention in greater detail.

BRIEF DESCRIPTION OF THE DRAWINGS

FIG. 1 shows a perspective representation of a first embodiment of an orthodontic device according to the invention;

FIG. 2 shows a perspective representation of the first embodiment of the device according to the invention in disassembled form;

FIG. 3 shows a perspective representation of a second embodiment of the device according to the invention;

FIG. 4 shows a perspective representation of a third embodiment of the device according to the invention;

FIG. 5 shows a perspective representation of the third embodiment of the device according to the invention in disassembled form;

DETAILED DESCRIPTION OF THE INVENTION

Figure 6:
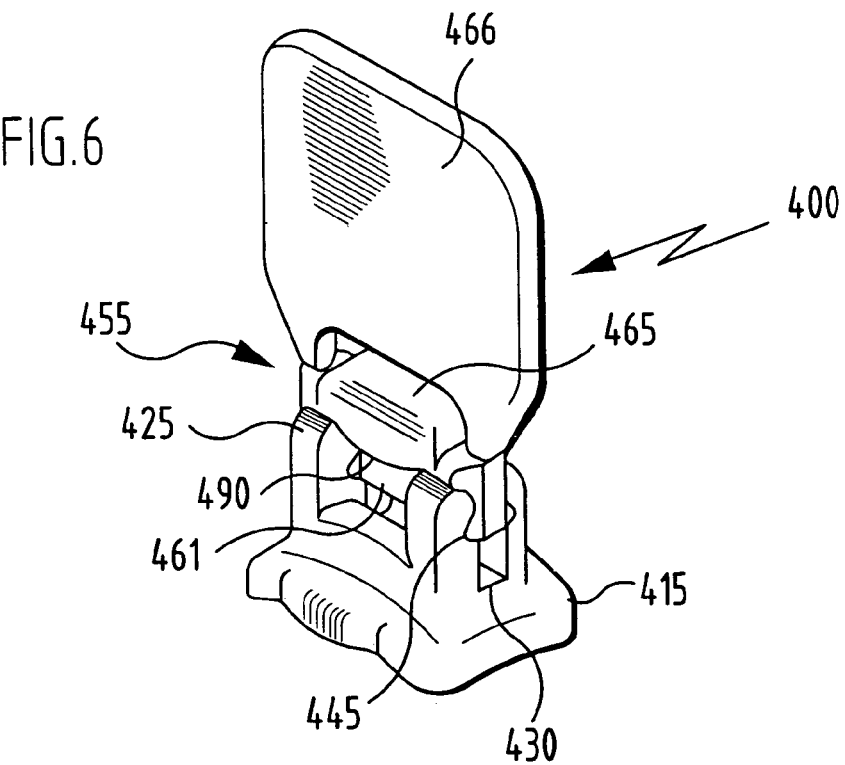
FIG. 6 shows a perspective representation of a fourth embodiment of the device according to the invention.
Figure 7:
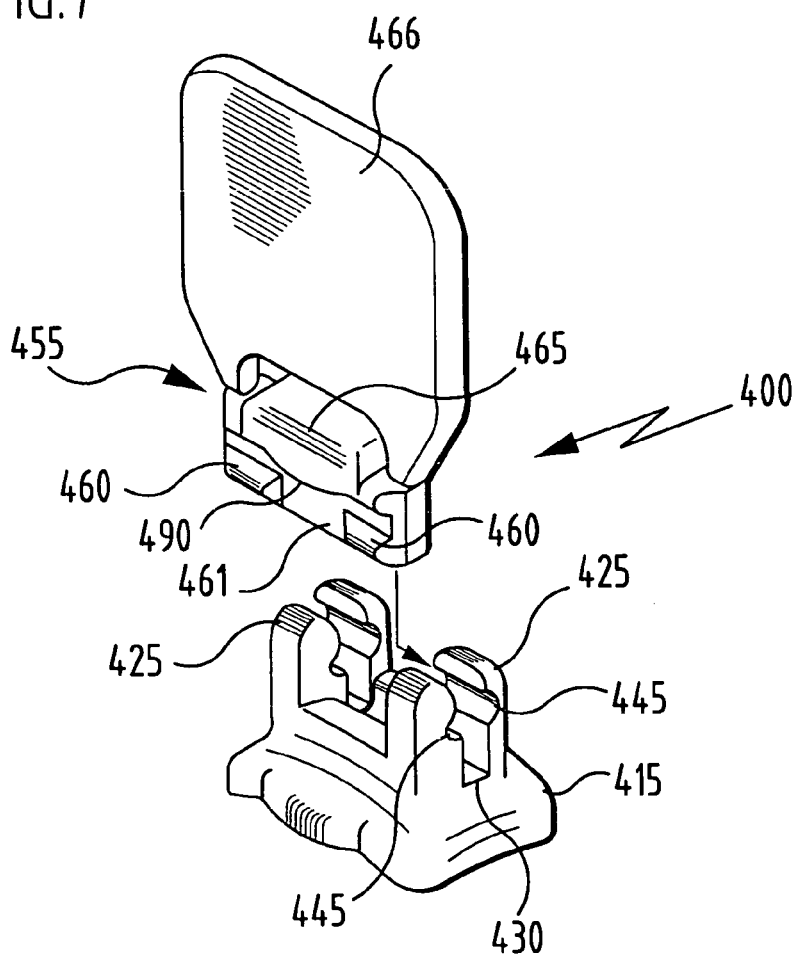
FIG. 7 shows a perspective representation of the fourth embodiment of the device according to the invention in disassembled form.

In FIGS. 1 to 5 and 8 and 9 the device according to the invention is designed as a bracket comprising a base with two pairs of bracket wings spaced from one another. However, such a design of the base is not imperative for the present invention. Accordingly, a suitable base for a bracket may, for example, have only one pair of bracket wings or no bracket wings at all or it may be of trapezoidal design. A further alternative is shown in FIGS. 6 and 7, where in the actual sense no bracket wings at all are provided for the insertion of ligatures.

A first embodiment of an orthodontic device according to the invention, generally designated by reference numeral 100, is shown in FIGS. 1 and 2 of the drawings. The device 100 is designed as a bracket with a base 115 having on its underside a curved surface 120 as base surface for fixing the device 100 to a tooth. At the side facing away from the curved surface 120, the base 115 forms two pairs of bracket wings 125 which are aligned in spaced parallel relation to each other.

An elongated rectangular slot 130 passes through the base 115 in the longitudinal direction thereof. The slot 130 is defined by a bottom surface 135 and by two side surfaces 140 arranged on either side of the bottom surface 135 and aligned in spaced parallel relation to each other.

The two opposed side surfaces 140 of the slot 130 each comprise a semicircular groove 145. These grooves 145 lie opposite each other, are aligned in parallel with each other and jointly form a positively locking guide in which a slide 155 is held insertably and detachably as cover element.

The slide 155 is pin-shaped and has two guide ribs 160 aligned parallel to each other as guide elements, which engage the positively locking guide formed by the grooves 145. The pin-shaped slide 155 has a triangular headpiece 165 at one end and is provided with a receiver 170 extending transversely to the guide ribs 160 for a securing element or as force application point for a conventional medical instrument for removal (not illustrated), with which the slide 155 is removable from or fixable to the base 115, for example, by means of a ligature or a wire as securing element.

The slide 155 of the orthodontic device 100 can be removed from the base 115 by pushing the slide 155 in the longitudinal direction of the slot 130, so that the base 115 and the slide 155 are then separate from each other, as shown in FIG. 2.

By placing or sliding the slide 155 into the positively locking guide formed by the grooves 145, the slot 130 of the base 115 is covered again in the longitudinal direction.

A second embodiment of the device, generally designated by reference numeral 200, is shown in FIG. 3 of the drawings. The slide 255 of the device 200 has a ring-shaped headpiece 265 by means of which the slide 255 is removable from the base 215, for example, by means of a hook-shaped medical instrument.

A third embodiment of the device, generally designated by reference numeral 300, is shown in FIGS. 4 and 5 of the drawings. The slide 355 of the device 300 comprises at each of the sides provided with the guide ribs 360 a recess 375 and a movable locking element 380 protruding beyond the guide ribs 360.

The locking element 380 comes to rest with a surface thereof against one of the pairs of bracket wings 325 of the base 315 and thus secures the slide 355 against displacement on the base 315.

By pressing the locking elements 380 into the recesses 375, the locking of the slide 355 on the base 315 is released, so that the slide 355 is removable from the base 315 in the longitudinal direction of the slot 330, and after removal, the slide 355 and the base 315 are separate from each other (FIG. 5).

A fourth embodiment of the device, generally designated by reference numeral 400, is shown in FIGS. 6 and 7 of the drawings. The slide 455 of the illustrated device 400 has an approximately I-shaped profile transversely to its longitudinal direction. The slide 455 is provided on either side thereof with two guide ribs 460 which are interrupted in the longitudinal direction and with a headpiece 465, which has on either side of the slot 430 a bulge 490 pointing in the direction of the guide ribs 460. The guide ribs 460 of the slide 455 are inserted in the positively locking guide formed by the grooves 445, and the bulges 490 engage the space between the pairs of bracket guides 425 of the base 415 and thus secure the slide 455 on the base 415 (FIG. 6). For improved handling of the slide 455, it has a grip element 466 which can be easily removed, for example, broken off, after insertion of the slide 455 into the grooves 445.

To release this locking of the slide 455, the bulges 490 must be guided past one of the pairs of bracket guides 425. The bulge 490, the headpiece 465 or the slide 455 in its entirety is, therefore, preferably made of an elastic material such as, for example, a plastic material.

Owing to the gaps 461 created by the interruption in the guide ribs 460 between the guide rib sections, the cover element 455 can be inserted on the buccal side into the slot 430 and brought with a small sliding movement in the longitudinal direction of the slot into its end position. In particular, this is advantageous when the orthodontic device 400 according to the invention is to be fixed at short distances from further such devices to the adjacent teeth of the patient. The displacement path for the cover element is thus considerably shortened in comparison with the embodiment of FIGS. 4 and 5.

Once the cover element 455 has reached the final position (FIG. 6), the grip element 466, which has so far served as holder, can be broken off or clipped off, thereby leaving only the actual slide 455 in the slot 430 of the bracket.

The slide 455 then remains inserted in the slot 430 during the treatment period and replaces hitherto conventional ligatures. When exchanging the archwire, the slide 455 can, of course, be removed from the slot and then replaced by a new cover element.

For this reason, the brackets of FIGS. 6 and 7 do not have the otherwise standard bracket wings.

Figure 8:
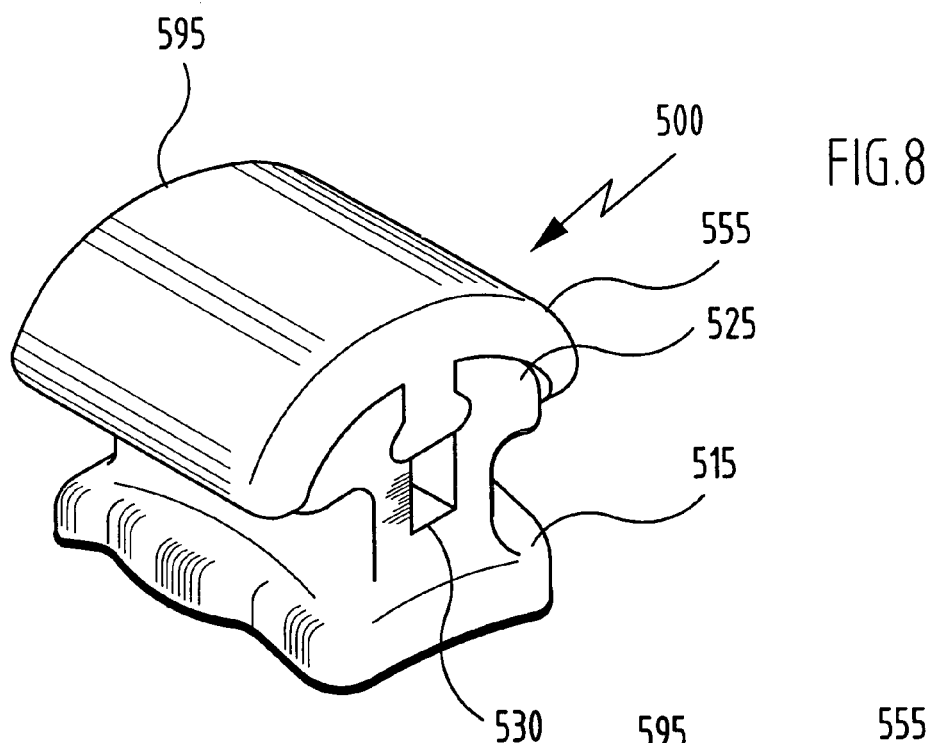
FIG. 8 shows a perspective representation of a fifth embodiment of the device according to the invention.
Figure 9:
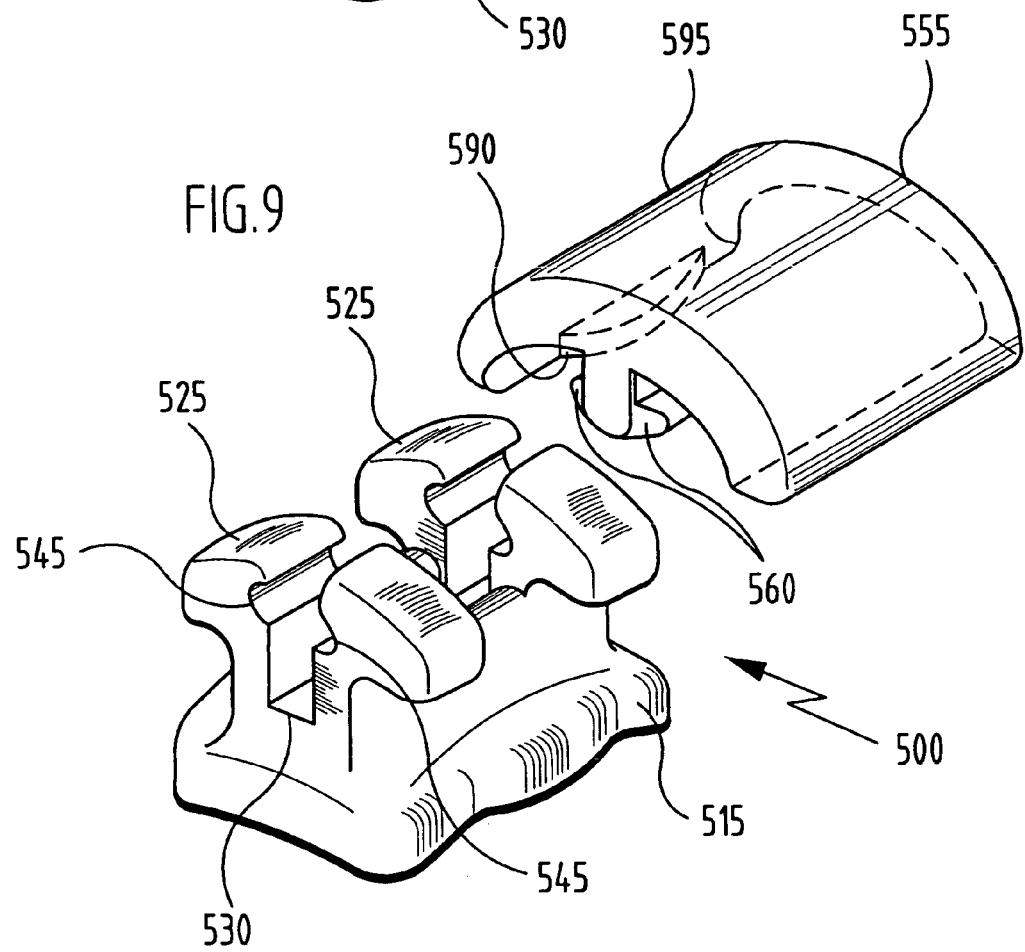
FIG. 9 shows a perspective representation of the fifth embodiment of the device according to the invention in disassembled form.

A fifth embodiment of the device, generally designated by reference numeral 500, is shown in FIGS. 8 and 9 of the drawings.

The slide 555 of the device 500 is T-shaped and has a curved cover 595 as veneer element, with a projection 590 provided on its inner surface.

In this embodiment the guide ribs 560 of the slide 555 also engage the positively locking guide formed by the grooves 545, and the cover 595 completely covers the bracket wings 525 from the side of the base 515 facing away from the curved surface 520 as well as the space located between these bracket wings 525. The cover 595 is preferably tooth-colored so as to conceal any aesthetically disadvantageous appearance of the base 515.

The projection 590 arranged on the inner surface of the cover 595 engages the space between the two pairs of bracket wings 525 and thus locks the slide 555 to the base 515.

In order to open the slot 530 of the device 500 depicted in FIG. 8, the projection 590 locking the slide 555 to the base 515 must be moved past one of the pairs of bracket wings 525. For this purpose it is advantageous for the slide 555 or the cover 595 or at least the projection 590 to be made of an elastic material.

Figure 10:
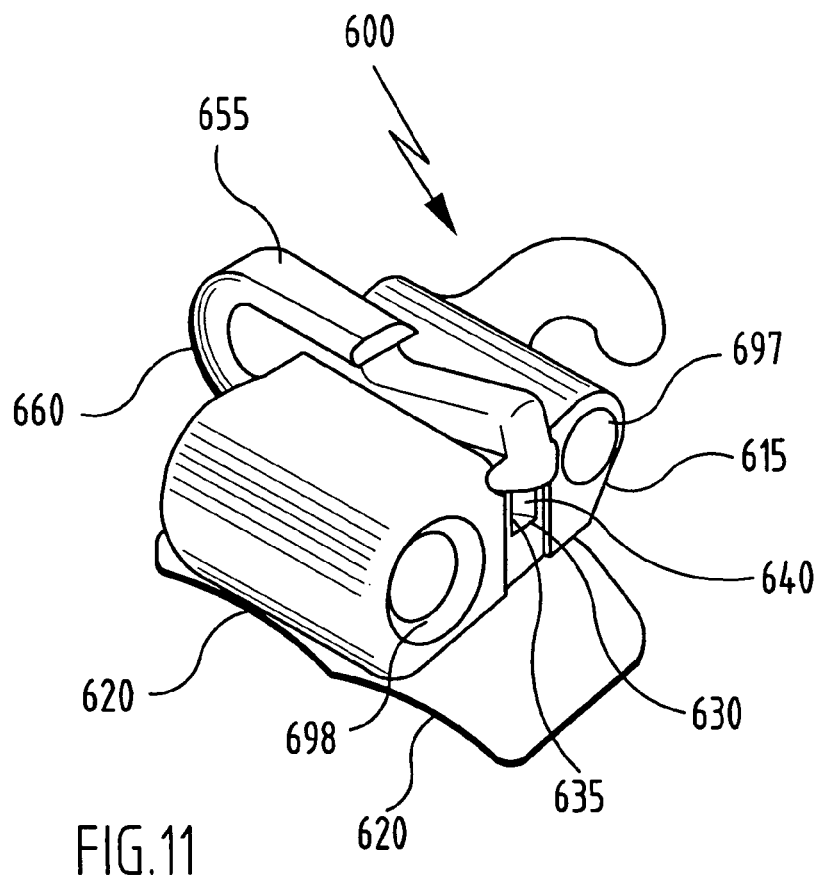
FIG. 10 shows a perspective representation of a sixth embodiment of the device according to the invention.
Figure 11:
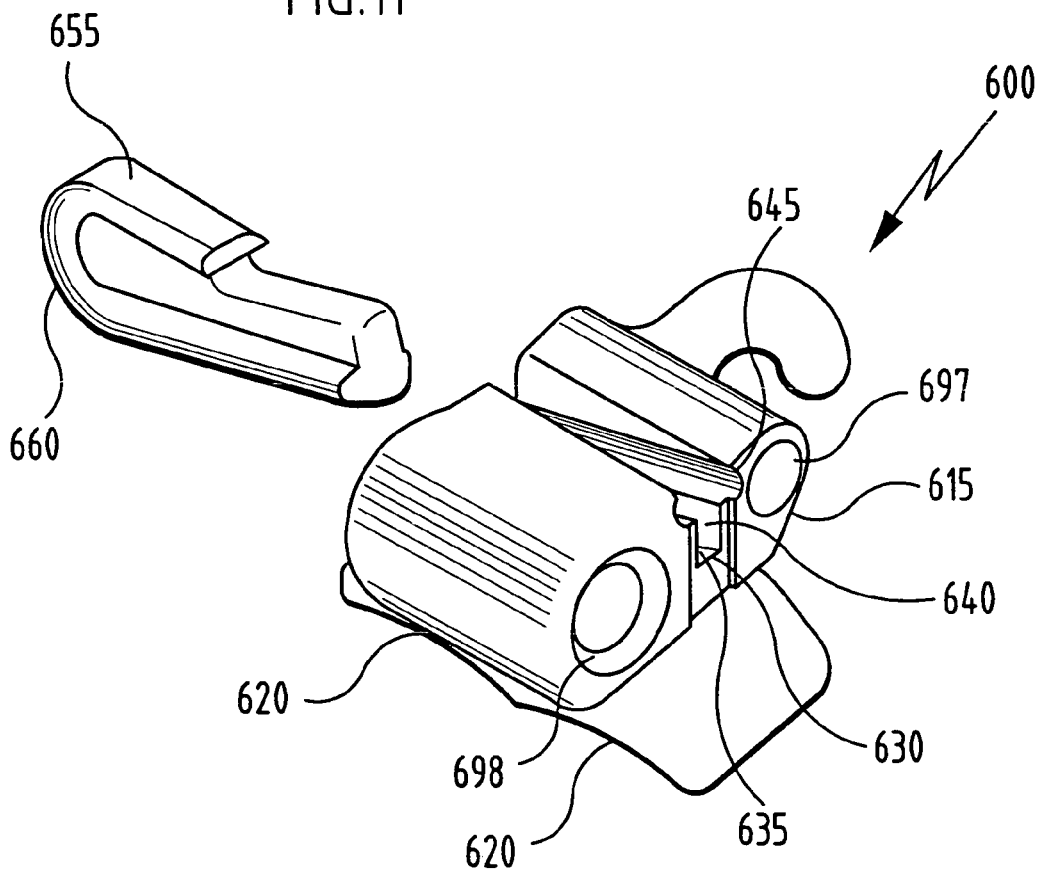
FIG. 11 shows a perspective representation of the sixth embodiment of the device according to the invention in disassembled form.

In FIGS. 10 and 11, the device according to the invention is designed as a buccal tube with a base comprising two through-bores aligned in parallel with each other. However, such a design of the base is not absolutely necessary, since for its suitability as buccal tube it is essential that it has a slot closed on the buccal side for reception of the end area of an archwire. Therefore, the base may, for example, also be of cube-shaped or trapezoidal design and have one or a plurality of through-bores or no through-bore.

An orthodontic device according to the invention, generally designated by reference numeral 600, in accordance with a sixth embodiment, is shown in FIGS. 10 and 11 of the drawings. The device 600 is designed as a buccal tube.

The base 615 has on its underside two curved surfaces 620 adjacent to each other for attachment of the device 600 to a tooth. The base 615 has two through-bores 697, 698 aligned parallel to each other, between which a rectangular slot 630 is arranged for reception of an archwire.

The slot 630 is defined by two parallel side surfaces 640 and by a bottom surface 635 perpendicular to these. The bottom surface 635 extends at an angle in relation to the longitudinal direction of the through-bores 697, 698. A semicircular elongated groove 645 is provided at each of the two side surfaces 640 of the slot 630. The grooves 645 are aligned parallel to each other and to the bottom surface 635 and jointly form a positively locking guide for reception of a slide 655.

The slide 655 is in the form of a small plate with a guide rib 660 bordering for the most part both sides thereof.

The slot 630 of the device 600 is covered by the slide 655 by the guide ribs 660 of the slide 655 being introduced into the positively locking guide formed by the grooves 645, and the slide 655 is held with a clamped fit in the positively locking guide on the base 615 by the guide ribs 660 which increase in thickness in a longitudinal direction of the slide 655.

Figure 12:
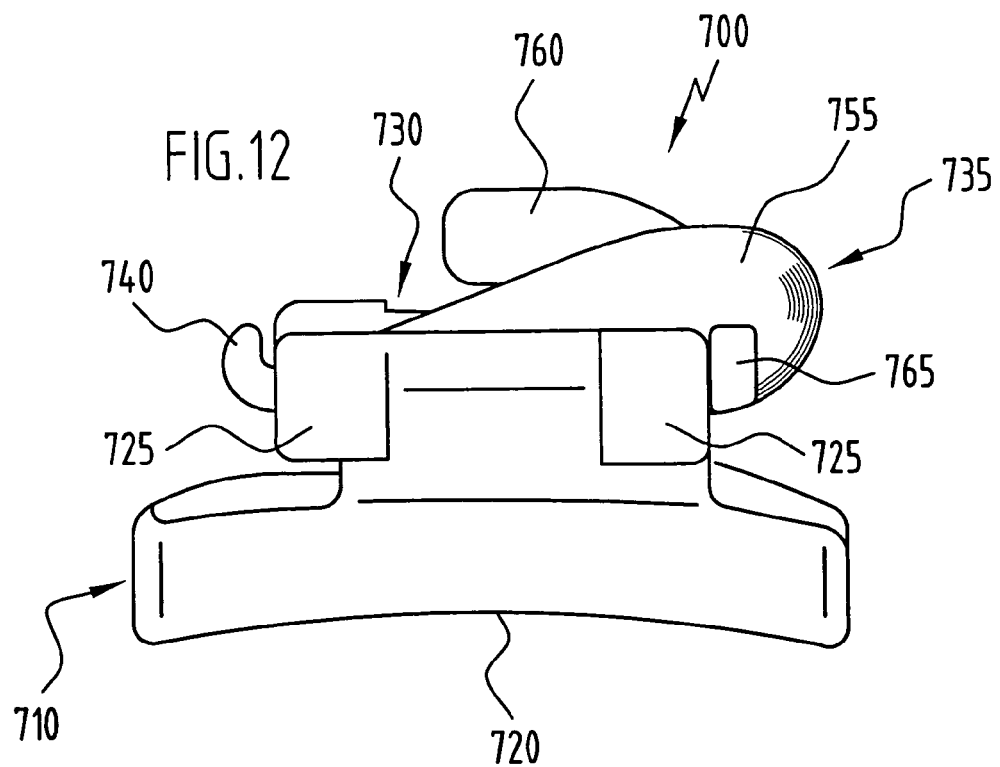
FIG. 12 shows a perspective representation in side view of a seventh embodiment of the device according to the invention.
Figure 13:
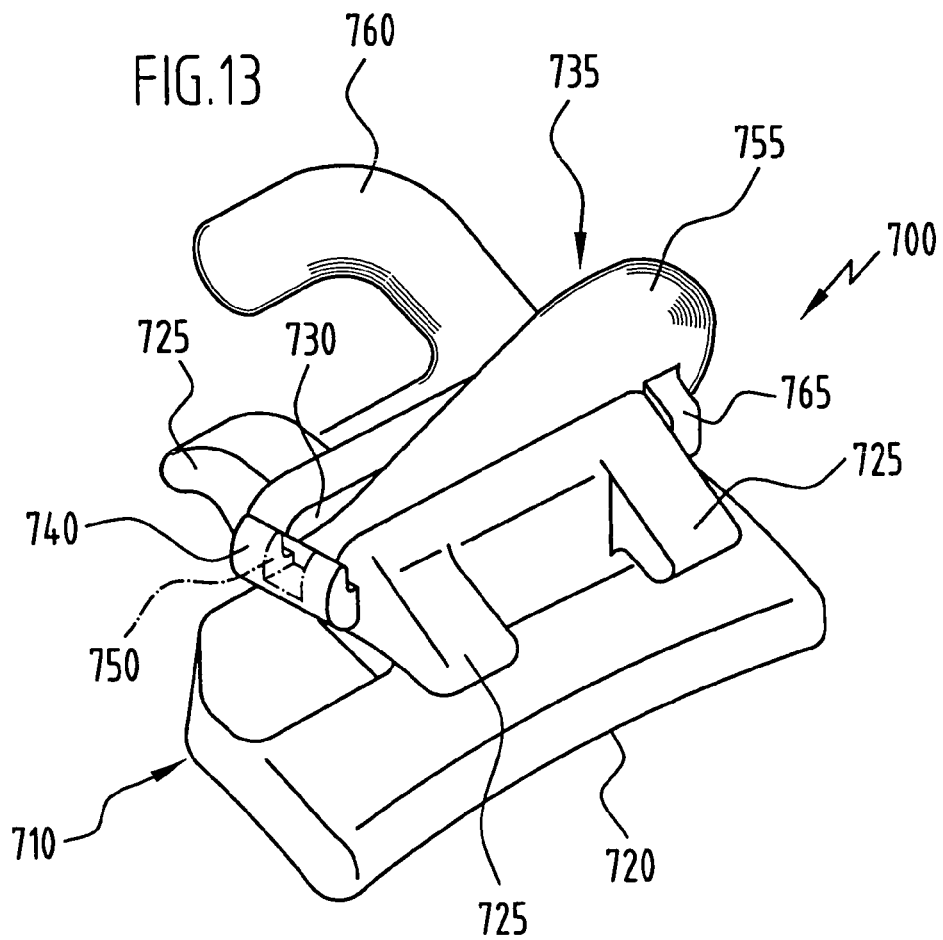
FIG. 13 shows a perspective representation of the seventh embodiment.

FIGS. 12 and 13 show a seventh embodiment of the device according to the invention, which is generally designated by reference numeral 700. The device 700 is designed as a bracket and comprises a base 710 with a base surface 720 and a slot 730 extending in the longitudinal direction and facing away from the base surface 720, in which a cover element 735 is slidably insertable. The basic design of the slot 730 and the corresponding design of the cover element 735 are also implemented here in analogy with the embodiments discussed hereinabove in order to obtain a positively locking guide.

The cover element 735 comprises a grip part 755 at which it can be easily introduced into the slot 730 of the base 710.

Since the device 700 is designed as a bracket, it comprises binding wings 725, via which an archwire (not shown herein) can be fixed later when the device 700 is used as a pure bracket. At its front end in the direction of insertion, the cover element 735 carries a projection 740, which initially protrudes forwards in a straight manner in the uninserted state, and, once the cover element 735 has reached its end position in the inserted state in the base 710, can be bent over upwards (alternatively, if desired, downwards) in the manner shown in FIGS. 12 and 13. The projection 740 thereby forms a mechanical securing element to prevent unintentional release and pulling out or sliding out of the cover element 735, which can be provided additionally or alternatively to the securing measures already described in conjunction with some of the above embodiments.

Alternatively, as indicated in broken representation in FIG. 13, the projection 740 can comprise a notch 750, which, alternatively to the upward or downward bending of the projection 740 or also additionally thereto, allows a deformation of the projection in the sense of an expanding in the horizontal direction.

Alternatively or additionally thereto, the projection 740 can also be designed so that it is connectable to the base 710 in a positively locking manner, for example, by spot welding or adhesive bonding, and this connection must then first be broken, for example, with an instrument, before the cover element 735 can be removed again.

This additional security measure, which can only be undone with an instrument, may be desired in some special cases of use, where owing to particular strain on the device 700, unintentional detachment of the cover element 735 during use would otherwise have to be anticipated.

The base 710 of the seventh embodiment comprises at the rearward side of the base 710 in the figures a small hook 760 which can be used as anchor point for further correction devices used together with the archwire and the brackets. The small hook 760 may be provided supplementarily or alternatively to a binding wing 725 on the base 710.

The cover element 735 preferably also comprises a stop 765 which defines the depth of insertion of the cover element 735 in the direction of the slot 730.

The invention claimed is:

1. Orthodontic device, comprising:
a base having a base surface for fixing the device to a tooth,
a slot for receiving an archwire, said slot being defined by
a bottom surface and two side surfaces arranged on either side of the bottom surface and aligned in substantially parallel spaced relation to each other, said slot extending in a substantially straight line through the base in a longitudinal direction of the base on a side thereof facing away from the base surface, and
a cover element for at least partially covering an open side of the slot facing the bottom surface, the side surfaces of the slot having a positively locking guide which is aligned substantially parallel in relation to the longitudinal direction of the slot, and the cover element being slidably and detachably held on the base in the positively locking guide,
wherein the positively locking guide is formed by two grooves disposed in said side surfaces of the slot facing each other and at a distance from the bottom surface of the slot, and the cover element is of flat configuration at the side facing the bottom surface of the slot and has two guide elements which are of complementary design to the grooves and engage the grooves in a positively locking manner.

2. Device in accordance with claim 1, wherein the grooves are disposed in the side surfaces so as to face each other directly.

3. Device in accordance with claim 1, wherein the grooves are aligned substantially parallel to the longitudinal direction of the slot.

4. Device in accordance with claim 1, wherein the grooves are aligned at an acute angle to the bottom surface of the slot.

5. Device in accordance with claim 1, wherein the slot has a rectangular cross section transversely to its longitudinal direction.

6. Device in accordance with claim 1, wherein in a fully inserted state, the cover element is secured with a clamped or pressed fit in the positively locking guide on the base.

7. Device in accordance with claim 1, wherein the cover element has a receiver for a securing element, and the cover element is securable to the base in a fully inserted state by the securing element.

8. Device in accordance with claim 1, wherein the cover element has a locking element for securing the cover element to the base in a fully inserted state.

9. Device in accordance with claim 1, wherein the cover element has a headpiece for gripping and removing the cover element.

10. Device in accordance with claim 9, wherein the headpiece comprises one of a hook or an eyelet for gripping and removing the cover element by means of a dental instrument.

11. Device in accordance with claim 1, wherein the guide elements are formed by two guide element sections which are arranged in spaced relation to each other in the longitudinal direction.

12. Device in accordance with claim 1, wherein the cover element has rounded edges on all sides thereof.

13. Device in accordance with claim 1, wherein the cover element has a veneer element for veneering the side of the base that faces away from the base surface.

14. Device in accordance with claim 13, wherein the veneer element is tooth-colored.

15. Device in accordance with claim 1, wherein the cover element has a grip element which is removable after the cover element has been positioned in the slot.

16. Device in accordance with claim 15, wherein the grip element is adapted to be broken off along weakened locations.

17. Device in accordance with claim 1, wherein the cover element has at a front end in a direction of insertion a projection which in an inserted state protrudes from the slot of the base.

18. Device in accordance with claim 17, wherein the projection is deformable in the inserted state.

19. Device in accordance with claim 18, wherein the projection is deformable so as to form a mechanical securing element.

20. Device in accordance with claim 18, wherein the projection is thermoformable.

21. Device in accordance with claim 18, wherein the projection has a notch or a slot and is expandable in an area of the notch or the slot so as to form a mechanical securing element.

22. Device in accordance with claim 17, wherein a part of the projection is joinable to the base with a substance-to-substance bond.

23. Device in accordance with claim 1, wherein the cover element is made of at least one of plastic and metal.

24. Device in accordance with claim 1, wherein the device is a bracket.

25. Device in accordance with claim 1, wherein the device is a buccal tube.

* * * * *